(12) United States Patent
de Meulenaer et al.

(10) Patent No.: US 9,102,553 B2
(45) Date of Patent: Aug. 11, 2015

(54) DEVICES AND METHODS FOR TREATING FLUIDS UTILIZED IN ELECTROCOATING PROCESSES WITH ULTRASOUND

(75) Inventors: Eric Cordemans de Meulenaer, Wezembeek (BE); Mario Swinnen, Paal (BE); Jan Reinier Gosker, Capelle aan den IJssel (NL); Baudouin Hannecart, Brussels (BE)

(73) Assignee: Solenis Technologies, L.P., Schaffhausen (CH)

( * ) Notice: Subject to any disclaimer, the term of this patent is extended or adjusted under 35 U.S.C. 154(b) by 1806 days.

(21) Appl. No.: 11/629,758

(22) PCT Filed: Jun. 21, 2005

(86) PCT No.: PCT/US2005/021907
§ 371 (c)(1),
(2), (4) Date: Aug. 8, 2007

(87) PCT Pub. No.: WO2006/038926
PCT Pub. Date: Apr. 13, 2006

(65) Prior Publication Data
US 2008/0118396 A1    May 22, 2008

Related U.S. Application Data

(60) Provisional application No. 60/582,390, filed on Jun. 23, 2004.

(51) Int. Cl.
*C02F 1/36* (2006.01)
*A61L 2/025* (2006.01)
(Continued)

(52) U.S. Cl.
CPC . *C02F 1/36* (2013.01); *A61L 2/025* (2013.01); *C02F 1/30* (2013.01); *C02F 1/32* (2013.01); *C02F 1/74* (2013.01); *C02F 2103/16* (2013.01); *C02F 2303/04* (2013.01)

(58) Field of Classification Search
CPC .................................. C02F 1/36; A61L 2/025
USPC .................................................. 422/292, 300
See application file for complete search history.

(56) References Cited

U.S. PATENT DOCUMENTS

| 2,163,649 A | 6/1939 | Weaver |
| 2,717,874 A | 9/1955 | Verain |

(Continued)

FOREIGN PATENT DOCUMENTS

| DE | 4407564 | 9/1995 |
| DE | 4430587 | 2/1996 |

(Continued)

OTHER PUBLICATIONS

Hua I et al., "Optimization of Ultrasonic Irradiation as an Advanced Oxidation Technology," Environ. Sci. Technol. vol. 31, No. 8, pp. 2237-2243, Aug. 1997.

(Continued)

*Primary Examiner* — Regina M Yoo
(74) *Attorney, Agent, or Firm* — Joanne Rossi; Michael Herman

(57) ABSTRACT

A method for treating electrocoating fluids involves exposing the electrocoating fluid to high-frequency ultrasound while emitting microbubbles into the electrocoating fluid. In further embodiments, the method includes emitting electromagnetic radiation into the fluid. In other embodiment, the method includes routing electrocoating fluid into a compartment. An apparatus for treating electrocoating fluids comprises a compartment (2) configured to hold electrocoating fluid, at least one ultrasound emitter (1) configured to emit high-frequency ultrasound (4) into the compartment (2), and a microbubble emitter (3) configured to emit microbubbles (5) into the compartment (2). In further embodiments, the apparatus may be in fluid communication with an external electrocoating bath. In other embodiments, the apparatus may include an electromagnetic radiation emitter (12), which may emit visible light into the compartment.

9 Claims, 1 Drawing Sheet

(51) Int. Cl.
*C02F 1/30* (2006.01)
*C02F 1/32* (2006.01)
*C02F 1/74* (2006.01)
*C02F 103/16* (2006.01)

(56) References Cited

U.S. PATENT DOCUMENTS

| | | | |
|---|---|---|---|
| 3,672,823 | A | 6/1972 | Boucher |
| 4,003,832 | A | 1/1977 | Henderson et al. |
| 4,076,617 | A | 2/1978 | Bybel et al. |
| 4,144,722 | A | 3/1979 | Mattwell |
| 4,211,744 | A | 7/1980 | Boucher |
| 4,231,850 | A * | 11/1980 | Kato ............................. 204/482 |
| 4,568,438 | A * | 2/1986 | Lauke ........................... 204/479 |
| 4,602,184 | A | 7/1986 | Meitzler |
| 4,820,260 | A | 4/1989 | Hayden |
| 4,879,045 | A | 11/1989 | Eggerichs |
| 4,961,860 | A | 10/1990 | Masri |
| 4,971,991 | A | 11/1990 | Umemura |
| 5,130,031 | A | 7/1992 | Johnston |
| 5,130,032 | A | 7/1992 | Sartori |
| 5,149,319 | A | 9/1992 | Unger |
| 5,198,122 | A | 3/1993 | Koszalka et al. |
| 5,215,680 | A | 6/1993 | D'Arrigo |
| 5,224,051 | A | 6/1993 | Johnson |
| 5,380,411 | A | 1/1995 | Schlief |
| 5,409,594 | A * | 4/1995 | Al-Jiboory et al. ........... 205/148 |
| 5,523,058 | A | 6/1996 | Umemura |
| 5,558,092 | A | 9/1996 | Unger et al. |
| 5,611,993 | A | 3/1997 | Babaev |
| 5,632,886 | A | 5/1997 | Staniec |
| 5,827,204 | A | 10/1998 | Grandia et al. |
| 5,971,949 | A | 10/1999 | Levin et al. |
| 5,997,812 | A | 12/1999 | Burnham et al. |
| 6,068,857 | A | 5/2000 | Weitschies et al. |
| 6,077,431 | A | 6/2000 | Kawanishi et al. |
| 6,113,558 | A | 9/2000 | Rosenschein et al. |
| RE36,939 | E | 10/2000 | Tachibana et al. |
| 6,138,698 | A * | 10/2000 | Tanaka et al. ................. 134/184 |
| 6,308,714 | B1 | 10/2001 | Peterson et al. |
| 6,309,355 | B1 | 10/2001 | Cain et al. |
| 6,413,216 | B1 | 7/2002 | Cain et al. |
| 6,428,532 | B1 | 8/2002 | Doukas et al. |
| 6,506,584 | B1 | 1/2003 | Chandler et al. |
| 6,540,922 | B1 | 4/2003 | Cordemans et al. |
| 6,656,436 | B1 | 12/2003 | Sentagnes et al. |
| 6,736,979 | B2 | 5/2004 | De Meulenaer et al. |
| 7,048,863 | B2 | 5/2006 | Swinnen et al. |
| 2002/0111569 | A1 | 8/2002 | Rosenschein et al. |
| 2003/0136824 | A1 | 7/2003 | Simon |
| 2005/0003737 | A1 * | 1/2005 | Montierth et al. ................. 451/5 |
| 2005/0061355 | A1 * | 3/2005 | Berman et al. .................. 134/1.3 |
| 2006/0144801 | A1 | 7/2006 | Swinnen et al. |
| 2007/0000844 | A1 | 1/2007 | Swinnen et al. |

FOREIGN PATENT DOCUMENTS

| | | |
|---|---|---|
| DE | 19700164 | 7/1998 |
| EP | 0 577 871 | 1/1994 |
| EP | 0 619 104 | 10/1994 |
| EP | 0 680 779 | 11/1995 |
| EP | 0 515 346 | 2/1996 |
| EP | 0 661 090 | 6/1998 |
| EP | 0936187 | 8/1999 |
| EP | 0 633 049 | 9/1999 |
| EP | 1008556 | 6/2000 |
| GB | 1389291 | 4/1975 |
| JP | 58128113 | 7/1983 |
| JP | 5228480 | 9/1993 |
| JP | 5228481 | 9/1993 |
| JP | 5228496 | 9/1993 |
| JP | 5345192 | 12/1993 |
| JP | 7155756 | 6/1995 |
| WO | WO 80/00226 | 2/1980 |
| WO | WO 93/13674 | 7/1993 |
| WO | WO 98/10394 | 1/1998 |
| WO | WO 98/05595 | 2/1998 |
| WO | WO 00/02821 | 1/2000 |
| WO | WO 2005/005322 | 1/2005 |

OTHER PUBLICATIONS

Marmor, et al., "Tumor eradication and cell survival after localized hyperthermia induced by ultrasound," Cancer Research, vol. 39, pp. 2166-2171, (Jun. 1979).

Miller, et al., "Single strand DNA breaks in human leukocytes inducted by ultrasound in vitro," Ultrasound in Med. & Biol., vol. 15, No. 8, pp. 765-771, (1989).

Nyborg, W. L. And Ziskin, M. C. (Eds.), *Biological Effects of Ultrasound*, Churchill-Livingstone Inc., New York, pp. 23-33, (1985).

Phull, S. S. et al., "The Development and Evaluation of Ultrasound in the Biocidal Treatment of Water," Ultrasonics Sonochemistry, vol. 4, No. 2, pp. 157-164, Apr. 1997.

Wyllie, et al., "Apoptosis and the regulation of cell numbers in normal and neoplastic tissues: an overview," Cancer and Metastasis Reviews, vol. 11, pp. 95-103, (1992).

Petrier, Christian et al., "Sonochemical Degradation of Phenol in Dilute Aqueous Solutions: Comparison of the Reaction Rates at 20 and 487 kHz," J. Phys. Chem., pp. 10514-10520, 1994.

Umemura, S. et al., "Sonodynamic Treatment by Inducing Microbubble Reaction," J.E.M.U., No. 2/3, pp. 265-270, 19998.

Umemura, Shin-ichiro et al., "Mechanism of Cell Damage by Ultrasound in Combination with Hematoporphyrin," Jpn. J. Cancer Res., No. 81, pp. 962-966, Sep. 1990.

Yu et al., A Review of Research Into the Uses of Low Level Ultrasound in Cancer Therapy, Ultrasonics Sonochemistry 11, pp. 95-103, 2004.

Bohm et al., "Viability of Plan Cell Suspensions Exposed to Homogeneous Ultrasonic Fields of Different Energy Density and Wave Type," Ultrasonics 38, pp. 629-632, 2000.

Miller, Douglas J., "Effects of High Amplitude 1-MMHz Standing Ultrasonic Field on the Algae Hydrodictyon," IEEE, No. 2, 1986.

Vollmer, et al"Bacterial Stress Responses to 1-Megahertz Pulsed Ultrasound in the Presence of Microbubbles," Applied and Environmental Microbiology, p. 3927-3931, Oct. 1998.

* cited by examiner

DEVICES AND METHODS FOR TREATING FLUIDS UTILIZED IN ELECTROCOATING PROCESSES WITH ULTRASOUND

CROSS-REFERENCE TO RELATED APPLICATIONS

This application claims priority under 35 U.S.C. § 119(e) to U.S. Provisional Application Ser. No. 60/582,390, filed on Jun. 23, 2004.

BACKGROUND OF THE INVENTION

1. Field of the Invention

The present invention is directed to the decontamination of industrial fluids and, in particular, to the decontamination of fluids utilized in electrocoating processes through low power, high frequency, ultrasonic radiation.

2. Description of the Related Art

Electrocoating (e-coating) generally relates to a coating method in which an electrical current is utilized to deposit a coat to a object. As used herein, preferred embodiments often describe "e-coating" as a painting method, but the term "e-coating" is broad enough to cover any suitable coating methods.

Electrocoating works on the principle that oppositely charged particles attract each other. More specifically, an electrocoating system typically applies a DC charge to a metal part (or any part desired to be painted) immersed in a bath of oppositely charged paint particles. The paint particles are drawn to the metal part, and paint is deposited on the part, generally forming an even, continuous film over the surface, including crevices and corners, until the coating reaches the desired thickness. After the desired thickness is achieved, the part can be insulated, to stop the deposition of the paint particles by stopping the attraction.

A typical electrocoating system consists of a number of components that can help maintain line parameters. For example a rectifier usually supplies the DC electrical charge to the bath, so to enable coating of the immersed object. In addition, circulation pumps often maintain proper paint mix uniformity throughout the electrocoat bath. Furthermore, temperature control of the paint bath is typically provided by a heat exchanger and/or chiller. Electrocoating systems often employ tank filters to remove dirt particles that are introduced into the paint system. Typically, ultrafilters are used to control paint conductivity, produce permeate for rinsing, and allow for recovery of paint solids.

E-coating generally consists of numerous steps including: electrodeposition pre-treatment, electrodeposition, painting, bathing, rinsing, and post rinsing, each of which involves industrial fluids. Before e-coating, the metal pieces are generally treated in a phosphatizing process, and then rinsed.

Unfortunately, fluids utilized in electrocoating processes, especially water-based fluids, are susceptible to bacteria, algae, fungi, yeasts, molds and other microbial propagation. The charged media encountered in e-coat installations are prone to bacterial developments, due to the high surface/volume ratios of the solid particles present in the formulations as well as their high organic content. Biological contamination of these fluids can be costly and dangerous, thus, some biological control for these fluids is desired.

Industrial fluids utilized in electrocoating processes can include complex compositions, slurries, and emulsions, as well as neat or filtered liquid. The liquid vehicle for these compositions is often demineralized or deionized water (DI) (See U.S. Pat. No. 5,393,390, to Freese, et al.). Coating compositions often contain various types of ingredients. For example, electrodeposition lacquers are often multicomponent aqueous emulsions or dispersions. Thus, it is advantageous to protect the formulations as well as the liquid medium itself.

In e-coating, one of the most abundant bacteria is the *Burkholderia Cepacia* which is a gram-negative bacterium. Human infection can be caused by *B. cepacia*, especially in patients with cystic fibrosis and chronic granulomatous disease, and can often be fatal.

It is important to note that biological fouling usually affects the entire e-coating system, including the circuitry, the filtration devices, as well as the coatings. Biological contamination of these fluids can also diminish the quality of the applied finish on parts, and increase both down time and maintenance costs. Biological fouling can also be deleterious for the quality of the finished product Biological contamination is usually associated with the formation of biofilm. Utilizing conventional treatments, it was often not possible to significantly reduce biofilm, thus, there is still a need for an effective biofilm removal from the circuit equipment and pipes. A number of patents, such as U.S. Pat. Nos. 5,971,757, 5,961,326, 5,749,726, and 5,204,004 teach the use of a variety of replaceable in-line water filters for trapping bacteria, such as biofilm sloughing.

To minimize these risks, hazards, and other negative effects of contaminated fluids utilized in electrocoating processes, many facilities add appreciable levels of various biocides to fluids utilized in electrocoating processes, to kill and inhibit the growth of microorganisms. In practice however, these agents are of limited usefulness. In addition to costing more money, there are limits on the amount of biocide which can be incorporated into an e-coating fluid without compromising the effectiveness of the fluid. Furthermore, these conventional techniques do not provide long term reduction of microbial counts in large industrial systems.

To obtain sustained and long usage of the electrocoating fluid, it is desirable that the treatment of the electrocoating fluid does not modify the electrocoating fluid or emulsion in its desired composition or characteristics. A major problem with biocides is that they can be detrimental to the efficacy and integrity of the e-coating fluid. Ultimately, the microorganisms overcome the biocides and the microbial degradation of electrocoating fluid and contaminants results in foul odors in the work environment.

In addition to using biocides, other facilities have used the following methods to treat e-coating fluids: the use of radioactive metals (e.g., U.S. Pat. No. 5,011,708 to Kelly, et al.), biofilm removal strategies (e.g., U.S. Pat. No. 6,183,649 to Fontana, and U.S. Pat. No. 5,411,666 to Hollis, et al.), physical methods, such as electrolysis (See U.S. Pat. No. 6,117,285 to Welch, et al. and U.S. Pat. No. 5,507,932 to Robinson), galvanic cell treatments (See U.S. Pat. No. 6,287,450 to Hradil, and U.S. Pat. No. 6,746,580 to Andrews, et al.), and pulsed light sterilization (See U.S. Pat. No. 6,566,659 to Clark, et al.).

Previous treatment methods have also used biocides to treat industrial installations used in e-coating. These installations often use filtering systems for the transfer and recirculation of fluids charged with clogged paint and coarse solid particles etc. Biological contamination of these filters was treated by the use of biocides. In situ cleaning systems (See U.S. Pat. No. 5,403,479 to Smith, et al.) of fouled microfiltration (MF) or ultrafiltration (UF) using semi-permeable hollow fiber membranes has also been used when flux decreased to an unacceptably low level.

Thus, conventional methods for the decontamination of e-coat fluids include membrane filtration to remove microorganisms, and/or the addition of chemicals, or other additives to kill and/or inhibit proliferating microorganisms in the fluid.

It is important to note that the liquid involved in e-coating processes is often mainly water. Thus, an industrial plant often needs to treat large amounts of demineralized and/or deionized water. There is typically a continuous replacement of spent water, due to evaporation, spillage, and drift. As contaminated deionized water is very corrosive, and the addition of anticorrosion chemicals is not always estimated as the best solution, there is still a need to cheaply and safely treat this deionized water, without significantly diminishing the effectiveness of the fluid.

While the use of high power, low frequency ultrasound has been proposed to treat surfaces locally for keeping them free of scaling, fouling and dirt (See U.S. Pat. No. 5,386,397, to Urroz) there is still a need in the art to decontaminate fluids used in the e-coating processes.

It is also important to note that high solid content in fluids is usually detrimental for chemical, UV, or low frequency ultrasonic mechanical treatments. More specifically, the solids often act as sorbents or shields to the transmission of the irradiation. Thus, the opacity and heterogeneity of the medium is often a hindering factor for its decontamination under classical methods. For example, opacity of the medium is specifically detrimental to UV treatment.

Accordingly, there is a need in the art for an effective and new method of treating fluids utilized in electrocoating processes without the use of large amounts of biocides, and which can provide uniform protection, or substantially uniform protection with time.

SUMMARY OF THE INVENTION

In another embodiment, an apparatus for reducing the presence of live microorganisms in a electrocoating fluid is provided, including a compartment holding electrocoating fluid, an ultrasound emitter configured to emit ultrasound signals at a frequency higher than 100 kHz into the compartment, and a gas microbubble emitter configured to emit gas microbubbles having an average diameter of less than 1 mm into the ultrasound field in the compartment.

In another embodiment, a method of treating electrocoating fluid is provided, including collecting electrocoating fluid from a fluid routing circuit, routing the electrocoating fluid into a compartment, and simultaneously exposing the electrocoating fluid in the compartment to gas microbubbles and ultrasound of a frequency of 100 kHz or higher.

In yet another embodiment, an apparatus is provided including an electrocoating system, a electrocoating fluid circuit connected to the electrocoating system, a compartment configured to hold electrocoating fluid through which the electrocoating fluid is routed, an ultrasound emitter configured to emit ultrasound signals at a frequency higher than 100 kHz into the compartment, and a gas microbubble emitter configured to emit gas microbubbles having an average diameter of less than 1 mm into the ultrasound field in the compartment configured to hold the electrocoating fluid.

DETAILED DESCRIPTION OF THE PREFERRED EMBODIMENT

Figure 1:
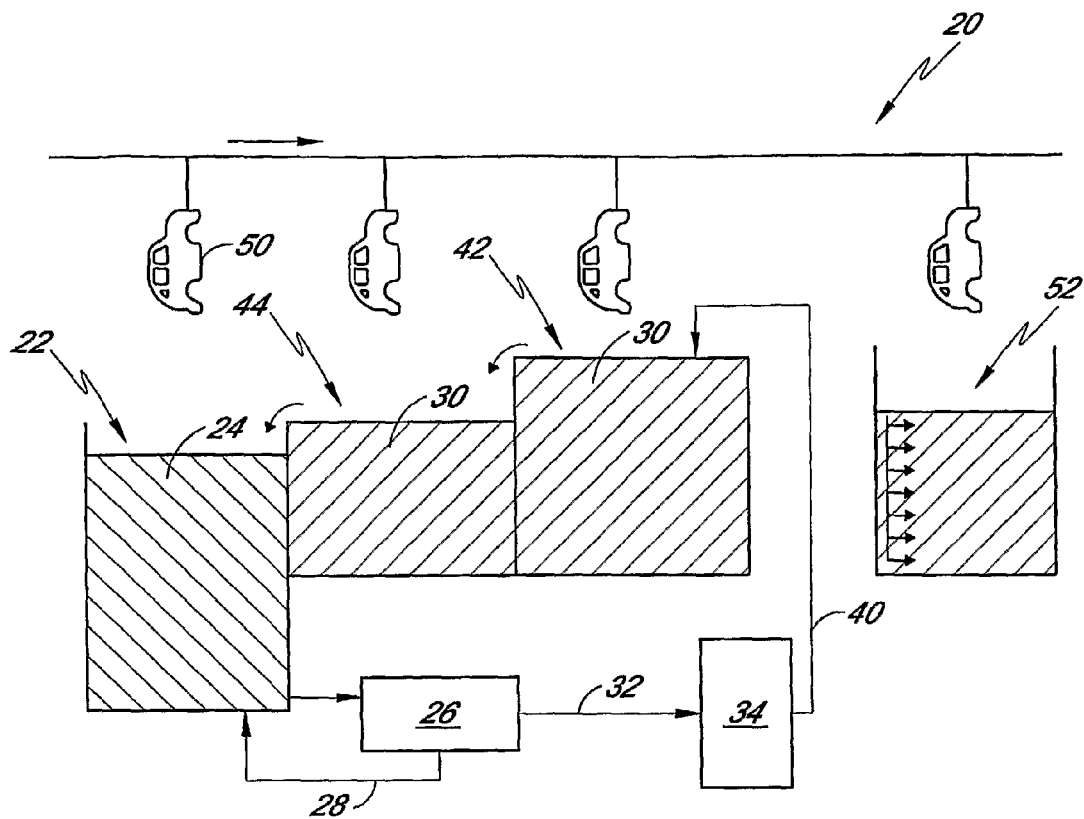
FIG. 1 is a drawing showing one possible example of the installation of the methods and devices described herein.

The following detailed description is directed to certain specific embodiments of the invention. However, the invention can be embodied in a multitude of different ways. In this description, reference is made to the drawings wherein like parts are designated with like numerals throughout.

The methods and devices described herein provide surprisingly effective and broad control of microorganisms in a number of e-coating systems. In preferred embodiments, methods and devices provided herein, relate to decontaminating fluids used in electrocoating processes with high frequency, low power, ultrasound. While the terms "decontaminate" or "treat" are both often used herein, it is noted that the disclosed methods and devices can be used to also prevent contamination in e-coating fluids.

In more specific embodiments, the methods and devices provided herein can be highly effective at removing biofilm present in industrial electrocoating circuits, extending the useful life of fluids utilized in electrocoating processes, and reducing or eliminating the risks posed to workers by heavily contaminated or biocide-treated fluids utilized in electrocoating processes.

One particular advantage of the methods and devices provided herein is that they can work in the presence of contaminants in the medium. Unlike conventional methods of treating e-coating fluids, the opacity and heterogeneity of the medium is not a significant hindering factor with the decontamination methods provided herein. Thus, in certain embodiments, the methods and devices provided herein can be applied to the treatment of heterogeneous water, compositions of low to high solid content, or liquid media.

In further embodiments, using the teachings herein, the solids can be treated indirectly. More specifically, the embodiments herein prevent biofilm from significantly forming on the surface of solids or, if biofilm is already present before the initiation of the high frequency/low power ultrasonic irradiation of the present technique, the embodiments herein significantly reduce the amount of biofilm.

In more particular embodiments, utilizing the devices and methods herein, the population level of microbes can be reduced to a level that does not pose a risk to workers, resulting in an improved quality to the working environment.

In other advantageous embodiments, the use of the methods and apparatuses herein can greatly extend the useful life and/or shelf-life of the e-coating fluid. In more particular aspects, the administered high frequency, low power, ultrasonic radiation does not significantly diminish the integrity or the effectiveness of the fluid.

In further embodiments, the teachings herein can also decontaminate particles which do not pass through the ultrasound compartment. For example, in industrial circuits, remote portions of the circuitry can be freed of biofilm, through the effect of the delayed biochemical mechanism of the disclosed methods.

In additional advantageous aspects, the costs for the disposal of contaminated fluids utilized in electrocoating processes and for electrocoating fluid replacement are substantially reduced. In addition, chemical pollution to the environment is minimized or avoided where processes are available for recycling used fluids.

In further embodiments, the methods and devices herein can be applied to treat solids, charged water, and major fluid mediums, without the use of biocides.

In additional embodiments, the methods and devices described herein can be effective on charged liquid media, and their various compositions, without altering their desired characteristics or inhibiting the efficacy of these compositions when used in e-coating processes.

In still further embodiments, the methods and devices provided herein can be used to treat pure deionized or demineralized water, or formulations containing deionized or demineralized water.

In preferred embodiments, the methods and devices described herein offer an environmentally-friendly solution to cope with the most stringent environmental and health regulations. In other preferred embodiments, the methods and devices described herein can yield a cost effective decontaminating effect that does not harm the environment more than prior art methods of treating e-coating fluids.

In more specific embodiments, the teachings herein are directed towards devices and methods which can neutralize, prevent the growth of, and remove microorganisms present in an electrocoating fluid. In further embodiments, the devices and methods provided herein can treat fluids utilized in electrocoating processes when those fluids are suspected of containing microorganisms, for example.

Electrocoating fluids with high solid content degrade with time, based in part on microbial (e.g., bacterial) growth and contamination. Accordingly, the embodiments herein encompass extending the useful life of electrocoating fluids by preventing degradation caused by microbes.

Devices and Methods

Embodiments of the devices described herein can be found in U.S. Pat. Nos. 6,540,922 and 6,736,979, to de Meulenaer et al. Methods of treating fluids utilized in electrocoating processes can be performed with the devices disclosed herein. One particular embodiment of a device that can be used for treating electrocoating fluid is represented in FIG. 1. In certain embodiments, the electrocoating fluid to be treated can contain microorganisms, including bacteria, viruses, fungi, protists, and the like, for example.

Depending on the polarity of the charge, electrocoating can typically be classified as either anodic or cathodic. The methods and devices herein can be used to treat fluids used in either anodic or cathodic electrocoating. In anodic electrocoating, the part to be coated is the anode with a positive electrical charge which attracts negatively charged paint particles in the paint bath. During the anodic process, small amounts of metal ions migrate into the paint film which can limit the performance properties of these systems. Their main use is typically for products in interior or moderately aggressive exterior environments.

In cathodic electrocoating, the part to be coated is given a negative charge, attracting the positively charged paint particles. Cathodic electrocoating generally applies a negative electrical charge to the metal part which attracts positively charged paint particles. Reversing the polarities used in the anodic process typically reduces the amount of iron entering the cured paint film and thus can enhance the properties of cathodic products. Cathodic coatings are high-performance coatings with excellent corrosion resistance and can be formulated for exterior durability.

Electrocoating technology can be further classified into two other categories: epoxies and acrylics. Both technologies are used extensively in anodic and cathodic systems. The following table, Table 1, provides the typical properties and end uses of these systems:

TABLE 1

|  | PROPERTIES | END USERS |
| --- | --- | --- |
| Anodic Epoxy | Low Cure | Agricultural Implements Automotive Parts Structural Steel |
| Anodic Acrylic | Color Control Gloss Control Interior Use Economical | Metal Office Furniture Air Diffusers Shelving Wire Screen & Hangers |
| Cathodic Epoxy | Corrosion Resistance Chemical Resistance | Automobiles & Parts Transformers Appliances |
| Cathodic Acrylic | UV Durability Corrosion Resistance Color Control | Lawn & Garden Agricultural Implements Automotive Wheels Trim Appliances |

The typically low cure attributes of anodic epoxies make these formulas good finishes for castings, engines, and temperature-sensitive substrates or assemblies. Heating, ventilation, and air conditioning parts are typically coated with anodic acrylic coatings. Anodic acrylic coatings are also used to coat electrical switchgear, which require not only color and gloss control, but also film hardness, chemical resistance, and corrosion protection.

Automobile bodies and automotive parts and accessories are some of the products typically coated via cathodic epoxy electrocoating. Cathodic acrylic coatings, also known for their chemical and alkali resistance, are commonly used to provide one-coat finishing for laboratory furniture, and lawn and garden equipment. The methods and devices taught herein can be used with the above listed electrocoating systems.

Typically the electrocoating process can be divided into four distinct sections pretreatment, electrocoat bath, post rinses, and oven baking. The methods and devices described herein can be used to treat electrocoating fluids used in any of these steps.

Generally, the pretreatments step comprises cleaning and phosphating the part to be coated in order to prepare the part for electrocoating. Cleaning and phosphating are often important in achieving the performance requirements desired by the end user. Iron and zinc phosphate are common materials used in pretreatment systems. Both spray and immersion stages can both be utilized in this section.

The electrocoat bath typically consists of 80-90% deionized water and 10-20% coating solids, such as paint. The deionized water acts as the carrier for the solids, which are usually under constant agitation. Paint solids generally consist of resin and pigment. Resin is typically the backbone of the final paint film and often provides corrosion protection, durability, and toughness. Pigments are typically used to provide color and gloss. The devices and methods herein can be used to treat both the water by itself and the water/paint solid composition.

In general, during an electrocoating painting process, paint is typically applied to a part at a controlled rate, which can be regulated by the amount of voltage applied. Once the coating reaches the desired film thickness, the part can be insulated, slowing the coating process down. As the part is removed from the bath, excess paint solids, commonly referred to as "drag out" or "cream coat," usually cling to the surface. These excess solids are then rinsed off to maintain efficiency and aesthetics. The rinse liquid used in these post rinses is typically returned to the tank for efficiency reasons. The devices and methods herein can be used to treat the rinse liquid.

After exiting the post rinses, the coated part typically enters the bake oven. In general, the bake oven crosslinks and cures the paint film to ensure maximum performance properties. Bake schedules typically utilize temperatures ranging from 180° F. to 375° F., depending on the technology being utilized.

FIG. 1 depicts an exemplary system 20 in which an embodiment of the present invention can be incorporated in order to treat fluid used in electrocoating. The electrocoating system includes an electrocoating bath 22 containing an electrocoating fluid 24, which in this embodiment contains roughly 20% paint solids. The electrocoating fluid 24 is routed to an ultrafiltration filter 26, which filters out the paint solids, sending them back to the electrocoating bath along path 28. The remaining component of the electrocoating fluid, which in this case is deionized water 30, is routed along a path 32 to an ultrasound/microbubble device 34, such as that discussed in greater detail below with respect to FIG. 1.

The ultrasound/microbubble device 34 is then used to treat the deionized water, as discussed below, and the treated deionized water is then routed along a path 40 to a rinse bath 42. In the system discussed with respect to FIG. 2, it can be seen that the deionized water 30, which serves as the rinse liquid, is permitted to spill over from the rinse bath 42 to a second rinse bath 44, and from there is permitted to spill into the electrocoating bath 22.

Figure 2:
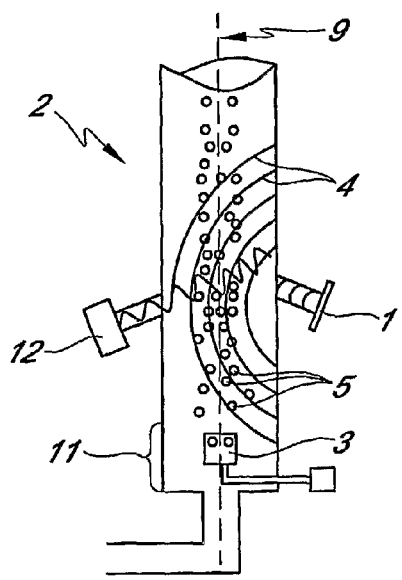
FIG. 2 is a drawing showing one embodiment of an ultrasound/microbubble device described herein.

With respect to FIG. 2, it can be seen that a series of objects 50 to be treated can be moved through a series of baths in order to perform the electrocoating process. An object 50, which has preferably been pretreated, is first lowered into electrocoating bath 22, and then removed. Post rinses are then performed by lowering the object into rinse baths 44 and 42, sequentially. The deionized water 30 is treated by the ultrasound/microbubble device 34, and the treated water will gradually flow from the upper rinse tank 42 down to the electrocoating bath 22, at which point it can be removed and treated again. It can also be seen that successive rinse baths, such as rinse bath 52, can be utilized when necessary, and that rinse baths may include flowing or otherwise agitated fluid, as depicted with respect to rinse bath 52.

Electrocoating is utilized in a variety of industrial market segments. Each of these markets has specific performance requirements, leading to a number of electrocoat technologies formulated to meet their needs. Electrocoating has also become an accepted finishing method for new applications, such as specialty clear finishes over aluminum; brass and zinc plating; extremely low-gloss coatings for military and photographic applications; chemical-resistant coatings; and transparent, metallic-type finishes over nickel or zinc plating.

The devices and methods herein can be used to treat electrocoating fluid used in any accepted or future application. The following table, Table 2, provides examples of specific applications of electrocoating that the devices and methods can be used with.

TABLE 2

Applications of Electrocoating in the Industrial Marketplace

| End Use | Properties Added By Electrocoat |
|---|---|
| Agricultural Equipment | High Gloss, Color Control, Weatherability, Corrosion Resistance |
| Appliance | Corrosion and Stain Resistance, Color Control in Recessed Areas |

TABLE 2-continued

Applications of Electrocoating in the Industrial Marketplace

| End Use | Properties Added By Electrocoat |
|---|---|
| Automobiles | Corrosion and Chip Resistance, Weatherability |
| Automotive Parts | Corrosion, Chemical and Chip Resistance |
| Brass, Gold, Nickel, Aluminum | Aesthetic Quality and Corrosion Resistance |
| Can Coatings (Containers) | Barrier and Chemical Resistance, FDA-Approved, No Effect on Flavor |
| Electrical Switchgear | Corrosion Resistance and U.L. Approval |
| Fasteners | Corrosion and Edge Coverage |
| Heating, Ventilation, and Cooling | Corrosion Resistance, Color Control, and Weatherability |
| Laboratory Furniture | Chemical, Stain, and Corrosion Resistance, Color Control |
| Lawn and Garden | Corrosion Resistance and Weatherability |
| Printed Circuit Boards | Edge Coverage and Hardness |
| Shelving and Furniture | Color Control, Hardness, and Stain Resistance |
| Wheels | Corrosion and Chip Resistance, Weatherability |

In certain embodiments, the devices and methods provided herein can be used in either one or two-coat electrocoating processes. For the two-coat electrocoating process, the first coat is typically conductive epoxy electrocoat, which when baked provides a surface that can receive a second coat of either epoxy or acrylic electrocoat. Two-coat electrocoating was developed to allow for corrosion resistance without sacrificing UV durability, while also benefiting from the superior efficiencies of electrocoat. The two coat system is typically capable of providing long-term exterior durability and corrosion resistance in excess of two thousand salt spray hours. Typical examples of end uses for the two-coat process are transformers, marine engines, generators, and maintenance applications.

In further embodiments, the devices and methods provided herein can be used to treat fluids used in both clear coat electrocoating and bulk electrocoating processes. Clear coat electrocoating typically involves coating metals such as gold, silver, brass, nickel, copper, zinc, aluminum, or steel with both clear and tinted formulations. Bulk electrocoating is typically used to coat large volumes of small parts.

Referring to FIG. 2, the devices described herein can include a compartment 2. In certain embodiments, the compartment 2 is in the shape of a cylinder, while in alternate embodiments, the compartment 2 may have a rectangular cross-section. In further embodiments the compartment 2 can be in communication with a reservoir (not shown) which holds the electrocoating fluid to be treated. The term "reservoir" is to be construed broadly, and generally relates to an apparatus containing electrocoating fluid. In specific embodiments the devices provided herein are connected (e.g., via a side stream) through a sump to the recirculating electrocoating fluid. In further embodiments, the devices provided herein are not in communication with a reservoir and are directly connected to the electrocoating fluid to be treated.

In further embodiments, the compartment 2 contains (e.g., along its wall) one or more high-frequency ultrasound emitters 1 that emit ultrasound 4 into the compartment 2 (preferably into the center of this compartment 2). In other embodiments the container can also have one or more microbubble emitters 3 for emitting gas microbubbles 5, which are arranged so as to emit the gas microbubbles 5 into the ultrasound 4 field emitted in the compartment 2.

The term "microbubbles," as used herein, is intended to refer to gas bubbles with an average diameter of less than 1 mm. In some embodiments the diameter is less than or equal to 50 μm. In yet other embodiments the microbubbles have a diameter less than about 30 μm. In certain embodiments the microbubbles are selected from air, oxygen, and ozone microbubbles. To lower operating costs, it can be advantageous to use microbubbles that are not ozone microbubbles, such as air microbubbles.

The term "microorganisms" is synonymous with microbes and generally relates to pathogenic or non-pathogenic microorganisms which can give rise to harmful effects to electrocoating equipment (e.g., machinery, tools, etc.), man, mammals or any other animal. Such microorganisms can include both aerobic and anaerobic bacteria, viruses, protists (e.g., mold, algae), and the like, for example.

In specific embodiments, the methods and devices herein include low energy, high-frequency, ultrasound to treat an electrocoating fluid. The term "high frequency" is intended to refer to frequencies higher than 100 kHz and up to several MHz. In certain embodiments, the high frequencies used are between 200 kHz and 10 MHz. In various embodiments, the ultrasound frequency can be selected from between 200 kHz to 3 MHz. In another embodiment, the frequency used is between 200 kHz and 1.8 MHz.

In various embodiments of the methods and devices described herein, the microbubble emitter 3 for emitting gas microbubbles 5 is arranged at the base 11 of the compartment 2, (i.e., at the bottom of the compartment 2), such that the microbubbles move by rising naturally or by entrainment of the gas in the flow of the electrocoating fluid.

In still further embodiments, the devices and methods provided herein, neutralize, treat or prevent the growth of microorganisms in an electrocoating fluid. Although the present teachings are in no way to be limited by their precise mechanism of action, in more specific embodiments the devices provided herein can produce radicals such as $ROO^-$, $H^-$, $^-OH$, $OH$ and $HOO^-$. These radicals can also form $H_2O_2$, which along with the radicals, is toxic to microorganisms and can bring about their inactivation and/or destruction.

Advantageously, the energy required to produce these toxic species is reduced if the process is performed in the presence of microbubbles, as described herein.

It has been recently appreciated that the injection of microbubbles into the ultrasound field gives rise to an increase in the phenomenon of sonoluminescence, by superposition of the microbubbles onto the cavitation bubbles induced by the ultrasound, which multiplies the number of excited and toxic species. This phenomenon is observed on a macroscopic level when the ultrasound treatment is synergistically combined with the presence of microbubbles of suitable size.

The effect of direct irradiation (e.g., ultrasound, laser, light) on certain molecules (e.g., classical photosensitizers and sonosensitizers) is the generation of highly active oxygen species such as singlet oxygen, superoxide radicals, or fatty acid radicals, which can play an important role, in particular in biochemical processes resulting from oxidative stress, in bactericidal properties of the treated electrocoating medium. Specifically, a singlet oxygen can oxidize the various cell components, such as the proteins, lipids, amino acids and nucleotides, for example. The production of extremely active oxygenated species such as the superoxide radical or singlet oxygen can result in a series of biochemical reactions that are extremely toxic for bacterial, fungal, algal, and mold cells.

In additional embodiments, the devices and methods provided herein have the advantage that there is no need to devote the ultrasound to specific zones, since it is observed that the treatment system functions by diffusing the products formed in situ (for example: molecular messengers, ROS: (reactive oxygen species), radicals and $H_2O_2$) towards the reservoir 6 of the electrocoating fluid to be treated.

In further embodiments, the one or more ultrasound 4 emitters 1 in the devices described herein are oriented so to limit standing-wave phenomena. For example, in certain embodiments, one or more ultrasound emitters can be oriented obliquely relative to the axis 9 of the compartment 2 (e.g., at an angle to this axis 9) and relative to the flow of electrocoating fluid and to the flow of microbubbles 5 (See FIG. 2) This characteristic makes it possible for all the microbubbles 5 in the compartment 2 to be treated in a statistically identical manner, without creating stationary zones in the compartment 2. Accordingly, certain embodiments herein are directed to devices and methods that provide uniform treatment, or substantially uniform treatment, and protection over time.

According to other embodiments, the devices and methods described herein can include a light emitter 12 (i.e. an electromagnetic radiation emitter) which emits into the compartment 2 in the ultrasound 4 field, radiation, with a frequency that is mostly in the visible range. However, for certain applications, in order to remove certain specific microorganisms, it can be advantageous to emit electromagnetic radiation with a frequency that is mostly non-visible, as ultraviolet radiation (e.g., UVA, UVB or UVC type), infrared, laser, microwaves, and the like, for example.

In various embodiments, the teachings herein are directed towards devices which do not require additional chemical products (e.g., biocides, photosensitizers) to neutralize or prevent the growth of microorganisms in an electrocoating fluid. Other embodiments are directed towards devices and methods which do not require additional chemical products such as photosensitizers and/or sonosensitizers to neutralize, prevent the growth of, and/or remove cells from an electrocoating medium.

In some embodiments, the devices and methods provided herein can be used in conjunction with anti-microbial agents such as peroxides (See U.S. Pat. No. 5,684,053 to Spangler, U.S. Pat. No. 6,552,215 to Van De Bovenkamp-Bouwman, et al.), ozone (See U.S. Pat. No. 5,157,069 to Hitchems et al., U.S. Pat. No. 6,746,580 to Andrews, et al.), quaternary ammonium salts (See U.S. Pat. No. 5,416,210 to Sherba, et al.), alone or in synergistic biocidal compositions which are intended to provide more effective and broader control of microorganisms in various industrial systems (See U.S. Pat. No. 5,759,786 to Hsu). Sometimes, specific biocides are used to help protect water-soluble cellulose derivates from microbial attack (See U.S. Pat. No. 5,430,078 to Hoppe-Hoeffler, et al.)

While in some alternate embodiments the methods and devices herein can be used with additional chemical agents, such as biocides, photosensitizers, sonosensitizers and other agents described above, it is important to note that the effectiveness of the provided methods and devices in treating, preventing the growth of or neutralizing microorganisms is not dependent on the use of other chemicals, reagents, or drugs (e.g., biocides). Accordingly, the methods and devices described herein can be used without anti-microbial agents or any other chemical or reagent.

In other embodiments, the devices and methods described herein can include a pump or other devices for recirculating the electrocoating fluid, as well as devices for recovering the microorganisms present in the electrocoating fluid. Examples of devices for recovering the microorganisms, non-exclusively include apparatuses for filtration, centrifugation, and precipitation (such as cyclones, and the like). In certain embodiments, the pump and/or devices for recovery are arranged between the reservoir containing the electrocoating fluid, to be treated and the compartment 2.

In further embodiments, the electrocoating fluid can be collected through gravity flow, velocity flow, or trenches (e.g., conveyorized trenches). In specific embodiments, after the electrocoating fluid is collected, it can be treated according to the methods provided herein and recirculated throughout the electrocoating system.

The methods and devices herein can be used to treat practically any type of electrocoating fluid used with any suitable equipment (e.g., machine) capable of electrocoating metals, and the like, for example. Such electrocoating fluids utilized in electrocoating processes may include, but are not limited to, aqueous media, emulsions, dispersions or solutions. The methods and devices herein can be used to treat any suitable type of electrocoating fluid currently available or that will be available in the future. The term "electrocoating fluid" is to be construed broadly and generally relates to fluids used in any step in electrocoating processes.

Examples of fluids utilized in electrocoating processes that the methods and devices herein can treat, include, but are not limited to the fluids utilized in electrocoating processes disclosed in U.S. Pat. No. 6,689,459 to Chung, et al., U.S. Pat. No. 5,559,174 to Clark, U.S. Pat. No. 5,430,078 to Hoppe-Hoeffler, et al., U.S. Pat. No. 4,728,401 to Miyawaki et al.

In certain embodiments, the methods and devices herein can be used to treat solid charged fluids utilized in electrocoating processes, because electrodeposition lacquers (See U.S. Pat. No. 6,589,411 to Kimpel, et al.) are often multicomponent aqueous emulsions or dispersions (See U.S. Pat. No. 6,309,710 to Sapper, U.S. Pat. No. 6,274,649 to Ott, et al, U.S. Pat. No. 6,559,220 to Hille, U.S. Pat. No. 6,448,328 to Kappler, et al.) comprising: resins, polymers, co-solvents, wetting agents for pigments and/or vehicles, coalescing aids, defoamers, plasticizers, rust inhibitors, catalysts, initiators; auxiliary substances and other additives including: anti-oxidants, stabilizers, photo-initiators, radical initiators, UV-light absorbers (See U.S. Pat. No. 6,509,399 to Gupta, et al), pigments and/or fillers, pot-life extenders, biocides, fungicides, and algaecides. The compositions (e.g., pigment paste, dispersions) of the coating baths are such that solids content can reach as much as 20% by weight. (See U.S. Pat. No. 6,500,229 to, Roux, et al.).

Depending on the specific type of fluid utilized in electrocoating to be treated with the methods and devices herein, the fluid utilized in electrocoating can contain water, and one or more emulsifiers, chelating agents, coupling agents, viscosity index improvers, detergents, plasticizers, anti-weld agents, oiliness agents, surfactant wetting agents, dispersants, passivators, anti-foaming agents, corrosion inhibitors, or any other suitable additive, for example. In certain embodiments, the water used in electrocoating processes is deionized or demineralized. In other embodiments, the water used can include solid particles and chemicals, as for example within rinsing fluids used in the electrocoat plant.

In certain embodiments, the methods and devices provided herein can treat each electrocoating fluid used by a particular electrocoating equipment, regardless of whether the electrocoating equipment is using one or more types of fluids utilized in electrocoating processes, or is connected to one or more fluids utilized in electrocoating processes reservoirs. Based on the above-mentioned functions, fluids utilized in electrocoating processes can lead to longer equipment life, reduced thermal deformation of the treated piece, a better surface finish, and the like, for example.

In further embodiments, the devices and methods herein can be used in conjunction with one or more other methods that prevent microbial propagation including: centrifuging, filtering, aerating, cleaning the sump, maintaining proper concentration of electrocoating fluid, removing solids, and adding biocides, for example. Accordingly, in certain embodiments, the devices and methods herein relate to applying high-frequency ultrasound either before, after, or during one or more the above-mentioned treatment methods, or other anti-microbial treatments.

While the foregoing description details certain embodiments of the teachings herein, it will be appreciated, however, that no matter how detailed the foregoing appears in text, the devices and methods herein can be practiced in many ways. As is also stated above, it should be noted that the use of particular terminology when describing certain features or aspects of the teachings herein should not be taken to imply that the terminology is being re-defined herein to be restricted to including any specific characteristics of the features or aspects of the teachings herein with which that terminology is associated. The scope of the teachings herein should therefore be construed in accordance with the appended claims and any equivalents thereof.

What is claimed is:

1. An apparatus comprising:
    an electrocoating system, the electrocoating system comprising an electrocoating bath, wherein the electrocoating bath is configured to hold an electrocoating fluid and to coat an object immersed therein;
    an electrocoating fluid circuit connected to the electrocoating system;
    a compartment configured to hold the electrocoating fluid through which said electrocoating fluid is routed, wherein said compartment is separated from and in fluid communication with the electrocoating bath;
    an ultrasound emitter configured to emit ultrasound signals at a frequency higher than 100 kHz into said compartment; and
    a gas microbubble emitter configured to emit gas microbubbles into the ultrasound field in the compartment configured to hold the electrocoating fluid.

2. The apparatus of claim 1, further comprising an electromagnetic radiation emitter configured to emit electromagnetic radiation in the visible range into the ultrasound field.

3. The apparatus of claim 1, further comprising a filter disposed along the fluid circuit between the electrocoating bath and the compartment configured to hold electrocoating fluid, wherein the filter is configured to filter out solid particles from the electrocoating fluid before the electrocoating fluid is routed to the compartment.

4. An apparatus comprising:
    an electrocoating bath, wherein the electrocoating bath is configured to hold an electrocoating fluid and coat an object immersed therein;
    an electrocoating fluid circuit;
    a compartment configured to hold the electrocoating fluid through which said electrocoating fluid is routed, wherein said compartment is in fluid communication with the electrocoating bath via the electrocoating fluid circuit;
    an ultrasound emitter configured to emit ultrasound signals at a frequency higher than 100 kHz into said compartment; and
    a gas microbubble emitter configured to emit gas microbubbles into the ultrasound field in the compartment configured to hold the electrocoating fluid, wherein the emitter is configured to emit gas selected from the group comprising air and oxygen.

5. The apparatus of claim 4, further comprising an electromagnetic radiation emitter configured to emit electromagnetic radiation in the visible range into the ultrasound field.

6. The apparatus of claim 4, further comprising a filter disposed along the fluid circuit between the electrocoating bath and the compartment configured to hold electrocoating fluid, wherein the filter is configured to filter out solid particles from the electrocoating fluid before the electrocoating fluid is routed to the compartment.

7. An apparatus comprising:
- an electrocoating bath, wherein the electrocoating bath is configured to hold an electrocoating fluid and coat an object immersed therein;
- an electrocoating fluid circuit;
- a compartment configured to hold the electrocoating fluid through which said electrocoating fluid is routed, wherein said compartment is in fluid communication with the electrocoating bath via the electrocoating fluid circuit;
- an ultrasound emitter configured to emit ultrasound signals at a frequency higher than 100 kHz into said compartment without generating a stationary field phenomenon; and
- a gas microbubble emitter configured to emit gas microbubbles into the ultrasound field in the compartment configured to hold the electrocoating fluid.

8. The apparatus of claim 7, further comprising an electromagnetic radiation emitter configured to emit electromagnetic radiation in the visible range into the ultrasound field.

9. The apparatus of claim 7, further comprising a filter disposed along the fluid circuit between the electrocoating bath and the compartment configured to hold electrocoating fluid, wherein the filter is configured to filter out solid particles from the electrocoating fluid before the electrocoating fluid is routed to the compartment.

* * * * *